(12) United States Patent
Michaelis et al.

(10) Patent No.: US 7,820,652 B2
(45) Date of Patent: *Oct. 26, 2010

(54) REGIMEN FOR THE ADMINISTRATION OF RIFAMYCIN-CLASS ANTIBIOTICS

(75) Inventors: Arthur F. Michaelis, Devon, PA (US); Bernard E. Cabana, Montgomery Village, MD (US)

(73) Assignee: ActivBiotics Pharma, LLC, Tucker, GA (US)

( * ) Notice: Subject to any disclaimer, the term of this patent is extended or adjusted under 35 U.S.C. 154(b) by 1621 days.

This patent is subject to a terminal disclaimer.

(21) Appl. No.: 10/948,608

(22) Filed: Sep. 23, 2004

(65) Prior Publication Data

US 2005/0143409 A1 Jun. 30, 2005

Related U.S. Application Data

(60) Provisional application No. 60/505,855, filed on Sep. 24, 2003.

(51) Int. Cl.
| | |
|---|---|
| A61K 31/54 | (2006.01) |
| A61K 31/535 | (2006.01) |
| A61K 31/497 | (2006.01) |
| A61K 31/44 | (2006.01) |
| A01N 43/42 | (2006.01) |

(52) U.S. Cl. ............ 514/224.5; 514/229.5; 514/252.13; 514/291

(58) Field of Classification Search ............... 514/224.5, 514/229.5, 252.13, 291
See application file for complete search history.

(56) References Cited

U.S. PATENT DOCUMENTS

| | | | |
|---|---|---|---|
| 3,301,753 A | 1/1967 | Sensi et al. | |
| 3,338,888 A | 8/1967 | Bickel et al. | |
| 3,342,810 A | 9/1967 | Maggi et al. | |
| 3,884,673 A | 5/1975 | Olin | |
| 3,923,791 A | 12/1975 | Celmer | |
| 3,976,765 A * | 8/1976 | Nachtigal | ..................... 424/54 |
| 4,005,077 A | 1/1977 | Bickel et al. | |
| 4,017,481 A | 4/1977 | Marsili et al. | |
| 4,086,225 A | 4/1978 | Marsili et al. | |
| 4,164,499 A | 8/1979 | Rossetti et al. | |
| 4,165,317 A | 8/1979 | Rossetti et al. | |
| 4,188,321 A | 2/1980 | Maggi et al. | |
| 4,219,478 A | 8/1980 | Marsili et al. | |
| 4,226,765 A | 10/1980 | Marsili et al. | |
| 4,305,941 A | 12/1981 | Marsili et al. | |
| 4,341,785 A | 7/1982 | Marchi et al. | |
| 4,551,450 A | 11/1985 | Traxler | |
| 4,585,589 A | 4/1986 | Malabarba et al. | |
| 4,681,938 A | 7/1987 | Traxler | |
| 4,690,919 A | 9/1987 | Yamane et al. | |
| 4,859,661 A | 8/1989 | Kano et al. | |
| 4,876,258 A | 10/1989 | Kump et al. | |
| 4,983,602 A | 1/1991 | Yamane et al. | |
| 5,003,070 A | 3/1991 | Kump et al. | |
| 5,352,679 A | 10/1994 | Ferrieri et al. | |
| 5,547,683 A | 8/1996 | Yano et al. | |
| 5,786,349 A | 7/1998 | Yamashita et al. | |
| 5,786,350 A | 7/1998 | Occelli et al. | |
| 5,981,522 A | 11/1999 | Yamashita et al. | |
| 6,316,433 B1 | 11/2001 | Rose et al. | |
| 6,486,161 B1 | 11/2002 | Fujii et al. | |
| 6,566,354 B1 | 5/2003 | Rose et al. | |
| 2003/0165457 A1 | 9/2003 | Martin | |
| 2003/0203903 A1 | 10/2003 | Rose et al. | |
| 2003/0236265 A1 * | 12/2003 | Sayada | ................... 514/252.13 |
| 2004/0014750 A1 | 1/2004 | Michaelis et al. | |
| 2004/0034021 A1 | 2/2004 | Michaelis et al. | |
| 2004/0077533 A1 | 4/2004 | Sayada | |
| 2004/0106590 A1 * | 6/2004 | Eisenstein | .................... 514/183 |
| 2004/0126414 A1 | 7/2004 | Michaelis | |
| 2004/0157840 A1 | 8/2004 | Cabana et al. | |
| 2004/0176404 A1 | 9/2004 | Sayada | |

OTHER PUBLICATIONS

Coates et al. Nature Reviews: Drug Discovery, 2002, vol. 1, pp. 895-910.*
"Rifalazil PathoGenesis Plans Phase II Studies," *R&D Focus Drug News* (1997).
Dietze et al., "Safety and Bactericidal Activity of Rifalazil in Patients with Pulmonary Tuberculosis," *Antimicrobial Agents and Chemotherapy* 45(7):1972 (2001).
Dhople AM, "In Vivo Susceptibility of Mycobacterium Ulcerans to KRM-1648, A New Benzoxazinorifamycin, in Comparison with Rifampicin," *Arzneimittelforschung* 51(6):501 (2001).
Hosoe et al., "Pharmacokinetics of KRM-1648, a New Benzoxazinorifamycin, in Rats and Dogs," *Antimicrobial Agents and Chemotherapy* 40(12):2749 (1996).
Kissling et al., "Parenteral Rifampicin in Tuberculous and Severe Non-Mycobacterial Infections," *Chemotherapy* 28:229 (1982).
Martinez et al., "Hypersensitivity Reactions to Rifampin. Pathogenetic Mechanisms, Clinical Manifestations, Management Strategies, and Review of the Anaphylactic-like Reactions," *Mayo J. Medicine* (Baltimore) 78(6):361 (1999).
Yamamoto et al., "In Vitro Bactericidal and In Vivo Therapeutic Activities of a New Rifamycin Derivative, KRM-1648, Against Mycobacterium Tuberculosis," *Antimicrobial Agents and Chemotherapy* 40(2):426 (1996).
Yamamoto et al., "Activity of KRM-1648 Alone or in Combination with Both Ethambutol and Kanamycin or Clarithromycin Against Mycobacterium Intracellulare Infections in Beige Mice," *Antimicrobial Agents and Chemotherapy* 40(2):429 (1996).

* cited by examiner

*Primary Examiner*—Sreeni Padmanabhan
*Assistant Examiner*—Samira Jean-Louis
(74) *Attorney, Agent, or Firm*—David Bradin; Intellectual Property, Technology Law

(57) ABSTRACT

The invention features an ascending dose regimen for the administration of rifamycin-class antibiotics. The dosing regimen can be used to treat bacterial infections and diseases related to infection.

22 Claims, No Drawings

REGIMEN FOR THE ADMINISTRATION OF RIFAMYCIN-CLASS ANTIBIOTICS

CROSS-REFERENCE TO RELATED APPLICATIONS

The application claims benefit of U.S. Provisional Application No. 60/505,855, filed Sep. 24, 2003, which is incorporated herein by reference.

BACKGROUND OF THE INVENTION

The present invention relates to methods of treating bacterial infections.

The ability of many bacterial infections to remain dormant but still viable and capable of causing disease is a major problem in the treatment and control of bacterial infections. For example, a useful treatment for *M. tuberculosis* must be effective against four different populations of tubercle bacilli within a single individual: a) rapidly growing extracellular and intracellular bacilli, b) bacilli within macrophages in an acidic environment, c) slow growing bacilli within caseous material at a neutral pH, and d) dormant bacilli. The dormant populations are not generally susceptible to conventional drug treatment regimens. For example, conventional drug treatment will kill actively growing *M. tuberculosis* within days, but months of therapy are needed to fully eliminate the dormant bacilli. If therapy is stopped too soon, the remaining dormant bacilli can be re-activated, leading to development of active, communicable disease.

Rifamycin-class antibiotics (e.g., rifampin, rifabutin, rifapentine, rifalazil, and rifaximin) are often the drug of choice for the treatment of various bacterial infections. To prevent the spontaneous development of resistant bacterial strains, rifamycin-class antibiotics are often given in combination with other antibacterial drugs (e.g., isoniazid, pyrazinamide, ethambutol, or streptomycin). For example, rifampin and isoniazid given in combination for nine months is a standard therapy for *M. tuberculosis* infections.

Rifamycin-class antibiotics are potent inhibitors of prokaryotic DNA-dependent RNA polymerase, with little activity against the equivalent mammalian enzymes. This group of antibacterial agents consists of compounds that are composed of aromatic rings linked by an aliphatic bridge.

One rifamycin-class antibiotic is rifalazil. Although rifalazil was found to be effective against mycobacterium species, it has never been used as a therapeutic agent for treatment of mycobacterial diseases because at the daily dose regimen which was believed to be necessary to its efficacious antibacterial activity, rifalazil caused severe adverse reactions, including flu-like symptoms with severe headache, malaise, fever, back pain, myalgia, chills, dizziness, nausea, vomiting, body pain, and weakness. Additionally, the daily administration of rifalazil resulted in changes in blood cell counts, particularly in decrease of white blood cell count (leukopenia), absolute neutrophil count, and platelet count, as well as in decreased blood hemoglobin.

More recently, a once or twice-a-week dose regimen was found to be efficacious against mycobacterium species, as described in U.S. Pat. No. 6,316,433, hereby incorporated by reference. It was also found that a once-or twice-a-week dosing regimen reduced, but did not eliminate, the incidence of adverse reactions. Clinical trials employing a twice-a-week dosing regimen demonstrated a clear dose-related incidence in the number and severity of adverse reactions. The predominate adverse reaction was development of "flu-like" symptoms.

Similar adverse reactions have been reported for other rifamycin-class antibiotics. Adverse reactions to rifampin are described, for example, by Martinez et al., *Medicine* (Baltimore) 78:361 (1999). Many of the adverse reactions induced by rifampin have been considered allergic in origin. For example, the flu-like syndrome appears to be caused by immune complexes, although their athogenetic mechanisms are not fully elucidated.

SUMMARY OF THE INVENTION

The invention provides a dosing regimen for administering rifamycin-class antibiotics that can reduce the occurrence of adverse reactions. This new dosing regimen can be used to treat bacterial infections and diseases related to infection.

Accordingly, in a first aspect, the present invention features a method of treating a bacterial infection in a mammal by administering to the mammal a rifamycin-class antibiotic in an ascending dose regimen.

The ascending dose regimen can include initial administration of the rifamycin-class antibiotic at an average daily dose for 4 to 14 days, followed by two to four times this average daily dose for the subsequent following 4 to 14 days.

In one embodiment, the ascending dose regimen includes initial administration of the rifamycin-class antibiotic at an average daily dose for 4 to 14 days, followed by twice this average daily dose for 4 to 14 days, and then followed by four times the average daily dose for 4 to 14 days.

In another embodiment, the ascending dose regimen includes administering the rifamycin-class antibiotic at an average initial daily dose which is less than 80% of the average daily dose over two, three, four, or five subsequent dosing days.

In still another embodiment, the ascending dose regimen includes administering the rifamycin-class antibiotic at a dose administered on Day 1 that is less than 90%, 80%, 70%, 60%, 50%, 40%, 30%, 20%, or 10% of the dose administered on any of the next four dosing days.

For any of the regimens described herein, the rifamycin-class antibiotic ay be selected from the group consisting of rifalazil, rifampin, rifabutin, rifapentine, and rifaxamin, or can be any other rifamycin-class antibiotic.

Examples of ascending dose regimens include, without limitation, the administration of rifalazil at a dose of less than 25 mg per week for 1-2 weeks followed by greater than 25 mg per week thereafter, the administration of rifalazil at a dose of less than 10 mg per week for 1-2 weeks followed by greater than 10 mg per week thereafter, the administration of rifalazil at a dose of less than 5 mg per week for 1-2 weeks followed by greater than 5 mg per week thereafter, and the administration of rifampin, rifapentine, or rifabutine at a dose of less than 300 mg per week for 1-2 weeks, followed by greater than 300 mg per week thereafter.

Any of the methods described above are useful for the treatment of community-acquired pneumonia, upper and lower respiratory tract infections, skin and soft tissue infections, hospital-acquired lung infections, bone and joint infections, respiratory tract infections, acute bacterial otitis media, bacterial pneumonia, urinary tract infections, complicated infections, noncomplicated infections, pyelonephritis, intra-abdominal infections, deep-seated abcesses, bacterial sepsis, central nervous system infections, bacteremia, wound infections, peritonitis, meningitis, infections after burn, urogenital tract infections, gastro-intestinal tract infections, pelvic inflammatory disease, endocarditis, and other intravascular infections. The infections to be treated may be caused by Gram-positive bacteria. These include, without limitation, infections by, *Staphylococcus aureus, Staphylococcus epidermidis, Enterococcus faecalis, Enterococcus faecium, Clostridium perfringens, Clostridium difficile, Streptococcus pyogenes, Streptococcus pneumoniae*, other *Streptococcus* spp., and other *Clostridium* spp. More specifically, the infections may be caused by a Gram-positive coccus, or by a drug-resistant Gram-positive coccus. Exemplary Gram-positive cocci include, without limitation, *S.,aureus, S. epidermidis, S. pneumoniae, S. pyogenes, M. catarrhalis, C. difficile, H. pylori, Chlamydia* spp., and *Enterococcus* spp.

The methods described above can be used to reduce or eliminate the incidence of postoperative infections in patients undergoing surgical procedures or implantation of prosthetic devices.

Furthermore, the methods described herein are useful for treating an infection by multi-drug resistant bacteria. Resistant strains of bacteria include penicillin-resistant, methicillin-resistant, quinolone-resistant, macrolide-resistant, and/or vancomycin-resistant bacterial strains. The multi-drug resistant bacterial infections to be treated using the methods of the invention include, for example, infections by penicillin-, methicillin-, macrolide-, vancomycin-, and/or quinolone-resistant *Streptococcus pneumoniae*; penicillin-, methicillin-, macrolide-, vancomycin-, and/or quinolone-resistant *Staphylococcus aureus*; penicillin-, methicillin-, macrolide-, vancomycin-, and/or quinolone-resistant *Streptococcus pyogenes*; and penicillin-, methicillin-, macrolide-, vancomycin-, and/or quinolone-resistant enterococci.

The invention also features a method for reducing *C. pneumoniae* replication in macrophages or foam cells in a patient in need thereof by administering to a patient a rifamycin-class antibiotic using any of the above regimens in an amount effective to reduce *C. pneumoniae* replication in macrophages or foam cells in the patient.

The invention features a method for treating a persistent *C. pneumoniae* infection in macrophages or foam cells in a patient by administering to a patient a rifamycin-class antibiotic using any of the above regimens in an amount effective to treat the *C. pneumoniae* infection in macrophages or foam cells in the patient.

The invention further features a method for treating an infection by a Gram-positive coccus in a patient by administering to a patient a rifamycin-class antibiotic using any of the above regimens in an amount effective to treat the Gram-positive coccus. In one embodiment, the Gram-positive coccus is drug-resistant The invention also features a method for treating chronic gastritis, gastric ulcer, or duodenal ulcer associated with an infection of *H. pylori*, or preventing the disease or infection, in a patient. The method includes the step of orally administering to a patient a rifamycin-class antibiotic using any of the above regimens in an amount effective to treat the *H. pylori* infection. If desirable, a rifamycin-class antibiotic can be administered with a proton pump inhibitor (e.g., omeprazole, esomeprazole, lansoprazole, leminoprazole, pantoprazole or robeprazole), and/or bismuth preparation (e.g., colloidal bismuth subcitrate or bismuth subsalicylate).

The invention features a method for treating a patient diagnosed as being infected with a bacterium having a multiplying form and a non-multiplying form. This method includes the step of administering to the patient a rifamycin-class antibiotic using any of the regimens described herein, and (ii) a second antibiotic that is effective against the multiplying form of the bacterium, wherein the two antibiotics are administered in amounts and for a duration that together treat the patient.

In one preferred method of carrying out the foregoing method, the antibiotic that is effective against the multiplying form of the bacterium is administered in an amount and for a duration to reduce the number of bacteria in the patient to less than about $10^6$ organisms/mL. This typically takes from a few hours to one, two or three days, but may take as long as a week. After this has been achieved, the patient is then administered patient a rifamycin-class antibiotic using any of the regimens described herein in an amount and for a duration effective to complete the treatment of the patient. Antibiotics that are effective against the multiplying form of the bacterium include any of the antibiotics described herein.

The invention features a method for treating a human patient diagnosed as having a chronic disease associated with a bacterial infection caused by bacteria capable of establishing a cryptic phase. The method includes the step of administering a rifamycin-class antibiotic using any of the regimens described herein to the patient.

The invention features a method for treating the cryptic phase of a bacterial infection. This method includes the step of administering a rifamycin-class antibiotic using any of the regimens described herein to a patient. The administering is for a time and in an amount effective to treat the cryptic phase of the bacterial infection.

The invention features a method for treating a bacterial infection in a human patient by (a) treating the multiplying form of the bacteria by administering an antibiotic to the patient for a time and an amount sufficient to treat the multiplying form, and (b) treating the non-multiplying form of the bacteria by administering a rifamycin-class antibiotic using any of the regimens described herein to the patient, wherein the administering is for a time and in an amount effective to treat the non-multiplying form.

Preferably, the bacterial infection is caused by one of the following: *Chlamydia* spp. (e.g., *C. trachomatis, C. pneumoniae, C. psittaci, C. suis, C. pecorum, C. abortus, C. caviae, C. felis, C. muridarum*), *N. hartmannellae, W. chondrophila, S. negevensis*, or *P. acanthamoeba*.

The time effective to treat a cryptic phase or other non-multiplying form of a bacterium ranges from one day to one year. In certain instances, treatment can be for several weeks or months, or even extended over the lifetime of the individual patient, if necessary. For example, the duration of treatment may be at least 30 days, at least 45 days, at least 90 days, or at least 180 days. Ultimately, it is most desirable to extend the treatment for such a time that the non-multiplying form is no longer detectable.

The invention features a method for treating or preventing the development of an atherosclerosis-associated disease in a human patient. The method includes administering a rifamycin-class antibiotic using any of the regimens described herein to the patient, wherein the administering is for a time and in an amount effective to treat or prevent the development of the atherosclerosis-associated disease in the patient. The patient is typically diagnosed as having the atherosclerosis-associated disease (or being at increased risk of developing the disease) or as having macrophages or foam cells infected with *C. pneumoniae* prior to administering a rifamycin-class antibiotic in ascending doses.

The invention also features a method of reducing the level of C-reactive protein in a human patient in need thereof. This method includes administering a rifamycin-class antibiotic using any of the regimens described herein to the patient, wherein the administering is for a time and in an amount effective to reduce the level of C-reactive protein in the patient. In one embodiment, the patient has not been diagnosed as having a bacterial infection. In another embodiment, the patient has been diagnosed as having macrophages or foam cells infected with *C. pneumoniae*.

The invention features a method for reducing *C. pneumoniae* replication in macrophages or foam cells in a human patient in need thereof. This method includes administering a rifamycin-class antibiotic using any of the regimens described herein to the patient, wherein the administering is for a time and in an amount effective to reduce *C. pneumoniae* replication in macrophages or foam cells in the patient.

The invention also features a method for treating a persistent *C. pneumoniae* infection in macrophages or foam cells in a human patient. The method includes administering a rifamycin-class antibiotic using any of the regimens described herein to the patient, wherein the administering is for a time and in an amount effective to treat the *C. pneumoniae* infection in macrophages or foam cells in the patient.

The invention also features a method for treating a chronic disease associated with an infection of *C. pneumoniae*. The method includes administering a rifamycin-class antibiotic using any of the regimens described herein to the patient, wherein the administering is for a time and in an amount effective to treat the infection.

The invention further features a method for treating a human patient having antibiotic-associated bacterial diarrhea or an infection of *C. difficile*, or preventing the disease or infection in the patient. The method includes administering a rifamycin-class antibiotic using any of the regimens described herein to the patient, wherein the administering is for a time and in an amount effective to treat the infection. The method may be employed as an initial treatment of a patient having or being at risk for developing antibiotic-associated bacterial diarrhea or infection of *C. difficile*, or it may be employed to treat patients for whom the initial treatment (e.g., with metronidazole or vancomycin) has failed to fully treat the antibiotic-associated bacterial diarrhea or an infection of *C. difficile*. The method may be employed, for example, when the patient is colonized with *C. difficile* organisms that are resistant to one or more of metronidazole and vancomycin.

In any of the above regimens, the rifamycin-class antibiotic may be administered in conjunction with one or more additional agents such as anti-inflammatory agents (e.g., non-steroidal anti-inflammatory drugs (NSAIDs; e.g., detoprofen, diclofenac, diflunisal, etodolac, fenoprofen, flurbiprofen, ibuprofen, indomethacin, ketoprofen, meclofenameate, mefenamic acid, meloxicam, nabumeone, naproxen sodium, oxaprozin, piroxicam, sulindac, tolmetin, celecoxib, rofecoxib, aspirin, choline salicylate, salsalte, and sodium and magnesium salicylate) and steroids (e.g., cortisone, dexamethasone, hydrocortisone, methylprednisolone, prednisolone, prednisone, triamcinolone), antibacterial agents (e:.g., azithromycin, clarithromycin, erythromycin, gatifloxacin, levofloxacin, arnoxicillin, isoniazid, ethambutol, pyrazinamide, streptomycin, capreomycin, ethionamide, cycloserine, kanamycin, tobramycin, amikacin, or metronidazole), platelet aggregation inhibitors (e.g., abciximab, aspirin, cilostazol, clopidogrel, dipyridamole, eptifibatide, ticlopidine, or tirofiban), anticoagulants (e.g., dalteparin, danaparoid, enoxaparin, heparin, tinzaparin, or warfarin), antipyretics (e.g., acetaminophen), or lipid lowering agents (e.g., cholestyramine, colestipol, nicotinic acid, gemfibrozil, probucol, ezetimibe, or statins-such as atorvastatin, rosuvastatin, lovastatin simvastatin, pravastatin, cerivastatin, and fluvastatin). These additional agents may be administered within 14 days, 7 days, 1 day, 12 hours, or 1 hour of the rifamycin-class antibiotic, or simultaneously therewith. The additional therapeutic agents may be present in the same or different pharmaceutical compositions as the formulation of the rifamycin-class antibiotic. -When present in different pharmaceutical compositions, different routes of administration may be used. For example, a second agent may be administered orally or by intramuscular or subcutaneous injection. Agents that can be administered in conjunction with the rifamycin-class antibiotic include any of the agents described herein.

Using any of the ascending dose regimens described herein, the rifamycin-class antibiotic may be administered orally, transdermally, parenterally, topically, or by suppositories. Topical administration includes inhalation, buccal, and transdermal administration. Parental administration includes intravenous, intraperitoneal, subcutaneous, and intramuscular administration. Oral administration includes any one of the following formulations: tablets, capsules, powders, syrups and sustained release microcapsules.

In another aspect, the invention features a kit comprising a rifamycin-class antibiotic. The kit is packaged with a label or package insert providing instructions for the use of the rifamycin-class antibiotic, wherein the instructions describe administration of a rifamycin-class antibiotic in an ascending dose regimen.

The kit may be a prepackaged therapeutic regimen including a first dosage unit which includes a rifamycin-class antibiotic; a second dosage unit which includes a larger dose of rifamycin-class antibiotic than the first dosage unit; instructions for the administration of the first dosage unit prior to the second dosage unit; and a pharmaceutical dispensing container prefilled with the dosage units and incorporating the instructions.

The dosage units may include one or more tablets, pills, capsules, or caplets.

The container can have one of any number of forms, including, without limitation, a box with the dosages in bottles, a blister package, a box of individual blister packages, or a box of pouches.

The methods and kits described herein can also be used to generate information useful, for example, for increasing investment in a company or increasing consumer demand for the methods and/or kits.

The invention therefore features a method of increasing consumer demand for a therapeutic regimen or kit described herein. The method includes the step of disseminating information about the therapeutic regimen or kit.

The invention further features a method of increasing investment in a company seeking governmental approval for the sale of a therapeutic regimen or kit described herein. The method includes the steps of i) disseminating information about the therapeutic regimen or kit, and ii) disseminating information about the intent of the company to market the therapeutic regimen or kit.

Consumer demand for a pharmaceutical composition or kit described herein, along with instructions to administer the pharmaceutical composition using a regimen described herein, can be increased by disseminating information about the utility, efficacy, or safety of the therapeutic regimen or kit. Consumers include health maintenance organizations, hospitals, doctors, and patients. Typically, the information will be disseminated prior to a governmental approval for the sale of a composition, therapeutic regimen, or kit of the invention.

A company planning to sell a pharmaceutical composition or kit described herein, along with instructions to administer the pharmaceutical composition using a regimen described herein, can increase investment therein by disseminating information about the company's intention to seek governmental approval for the sale of and disseminating information about the therapeutic regimen or kit. For example, the company can increase investment by disseminating information about in vivo studies conducted, or planned, by the company, including, without limitation, information about the toxicity, efficacy, or dosing requirements of a therapeutic regimen or kit of the invention. The company can also increase investment by disseminating information about the projected date of governmental approval of a therapeutic regimen or kit of the invention.

Information can be disseminated in any of a variety of ways, including, without limitation, by press release, public presentation (e.g., an oral or poster presentation at a trade show or convention), on-line posting at a web site, and mailing. Information about the therapeutic regimen or kit can include, without limitation, a structure, diagram, figure, chemical name, common name, tradename, formula, reference label, or any other identifier that conveys the identity of the therapeutic regimen, or kit of the invention to a person.

By "in vivo studies" is meant any study in which a therapeutic regimen or kit of the invention is administered to a mammal, including, without limitation, non-clinical studies, e.g., to collect data concerning toxicity and efficacy, and clinical studies.

By "projected date of governmental approval" is meant any estimate of the date on which a company will receive approval from a governmental agency to sell, e.g., to patients, doctors, or hospitals, a therapeutic regimen or kit of the invention. A governmental approval includes, for example, the approval of a drug application by the Food and Drug Administration, among others.

By a "rifamycin-class" antibiotic is meant a compound composed of aromatic rings linked by an aliphatic bridge and having antibacterial properties. Rifamycin-class antibiotics of the present invention have a general structure as shown in formula I.

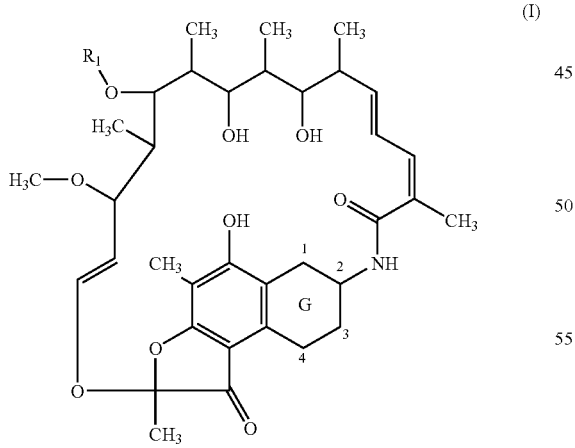

(I)

In formula I, each methine proton, methylene proton, and methyl proton is optionally substituted by —OH, $R_1$ represents a hydrogen atom or an acetyl group, and ring G is selected from formulas II-X.

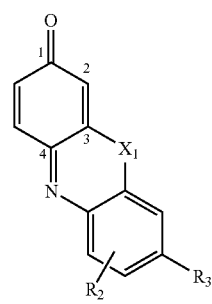

II

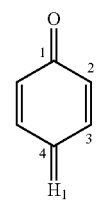

III

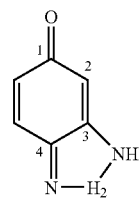

IV

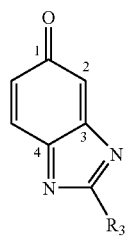

V

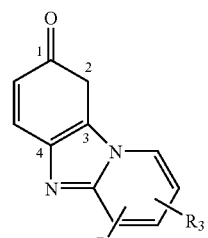

VI

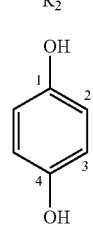

VII

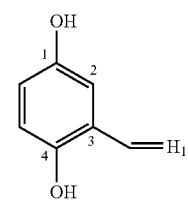

VIII

-continued

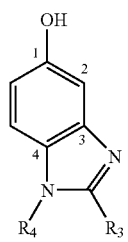

IX

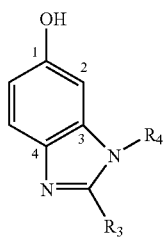

X

In the formulas above, $X_1$ represents N—CH$_3$, O, or S, $H_1$ represents an oxygen atom, or N—R$_3$, and $H_2$ represents a group expressed by one of formulas XI and XII.

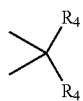

XI

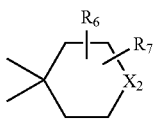

XII $R_2$ represents a hydroxyl group, a sulfhydryl group, a hydrogen atom, or an alkyl group having 1 to 3 carbon atoms. $R_3$ represents a hydrogen atom, an alkyl group having 1 to 10 carbon atoms, or a group expressed by one of formulas XIII-XV.

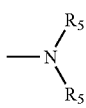

XIII

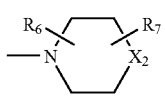

XIV

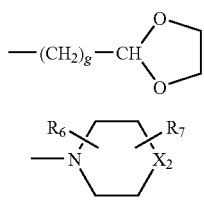

XV

Each $R_4$ is, independently, a hydrogen atom or an alkyl group having 1 to 7 carbon atoms. Each $R_5$ is, independently, an alkyl group having 1 to 7 carbon atoms, or two of $R_5$ in combination form a 3-8 membered cyclic system. In formula XIV, g represents an integer between 1 and 3. $R_6$ and $R_7$ are each, independently, a hydrogen atom or an alkyl group having 1 to 3 carbon atoms. $X_2$ represents an oxygen atom, a sulfur atom, a carbonyl group, or a group expressed by one of formulas XVI-XVIII:

XVI

XVII

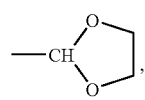

XVIII $R_8$ and $R_9$ are each, independently, a hydrogen atom, or an alkyl group having 1 to 3 carbon atoms, or $R_8$ and $R_9$, in combination with each other, represent —(CH$_2$)$_k$— in which k represents an integer between 1 and 4. In formula XVII, m represents 0 or 1. $R_{10}$ represents a hydrogen atom, an alkyl group having 1 to 7 carbon atoms, or —(CH$_2$)$_n$X$_3$ in which n represents an integer between 1 and 4. $X_3$ represents an alkoxy group having 1 to 3 carbon atoms, a vinyl group, or an ethynyl group.

Each of the alkyl groups having 1 to 3 carbon atoms expressed by $R^2$, $R^6$, $R^7$, $R^8$, and $R^9$ are each, independently, selected from methyl, ethyl, propyl, isopropyl, and cyclopropyl. The alkyl group having 1 to 7 carbon atoms expressed by $R^4$, $R^5$, and $R^{10}$ are each, independently, selected from a chain or cyclic alkyl group, examples of which include, without limitation, methyl, ethyl, propyl, isopropyl, cyclopropyl, butyl, isobutyl, sec-butyl, tert-butyl, cyclobutyl, cyclopropylmethyl, pentyl, isopentyl, sec-pentyl, tert-pentyl, cyclopentyl, cyclobutylmethyl, hexyl, 4-methylpentyl, cyclohexyl, 3-methylcyclopentyl, among others. The alkoxy group having 1 to 3 carbon atoms expressed by $X^3$ is selected from methoxy, ethoxy, propoxy, isopropoxy, and cyclopropoxy.

Examples of rifamycin-class antibiotics include rifampin, rifabutin, rifapentine, rifalazil, and rifaximin. Rifamycin-class antibiotics to be administered using the methods of the present invention are disclosed in, for example, U.S. Pat. Nos. 4,690,919; 4,983,602; 5,786,349; 5,981,522; and 4,859,661, each of which is incorporated herein by reference.

By "ascending dose regimen" or "ascending doses" is meant a regimen in which any of the following criteria are met: i) the average daily dose administered from the first day of treatment to day 4 is less than 80% of the average daily dose administered over the subsequent following four to fourteen days of administration; ii) the average initial daily dose is less than 80% of the average daily dose over five subsequent dosing days; or iii) the dose administered on Day 1 is less than 90% of the dose administered on any of the next four dosing days.

Desirably, ascending dose regimens comprise a regimen in which the average daily dose administered from the first day of treatment to 4, 6, 8, 10, 12, or 14 days is less than 80%, 70%, 60%, 50%, 40%, 30%, 20%, 10%, or 5% of the average daily dose administered over the following four to fourteen days of administration; a regimen in which the average initial daily dose is less than 80%, 70%, 60%, 50%, 40%, 30%, 20%, 10%, or 5% of the average daily dose over two, three, four, or five subsequent dosing days; or a regimen in which the dose administered on Day 1 is less than 90%, 80%, 70%, 60%, 50%, 40%, 30%, 20%, or 10% of the dose administered on any of the next four dosing days.

The term "administration" or "administering" refers to a method of giving a dosage of a pharmaceutical composition to a mammal, where the method is, for example, topical, oral, intravenous, intraperitoneal, or intramuscular. The method of administration can vary depending on various factors, such as the components of the pharmaceutical composition, site of the potential or actual disease, and severity of disease.

As used herein, the term "treating" refers to administering a pharmaceutical composition for prophylactic and/or therapeutic purposes. To "prevent disease" refers to prophylactic treatment of a patient who is not yet ill, but who is susceptible to, or otherwise at risk of, a particular disease. To "treat disease" or use for "therapeutic treatment" refers to administering treatment to a patient already suffering from a disease to improve or stabilize the patient's condition. Thus, in the claims and embodiments, treating is the administration to a mammal either for therapeutic or prophylactic purposes.

By "average daily dose" is meant the administered dose, in milligrams, of a rifamycin-class antibiotic per unit time. The average daily dose is calculated from the instructed regimen. For example, 25 mg twice weekly is an average daily dose of 7.14 mg/day (50 mg/7 days); 10 mg weekly followed by 20 mg weekly followed by 20 mg twice weekly is an average daily dose in week 1 of 1.43 mg/day (10 mg/7 days), in week 2 of 2.86 mg/day (20 mg/7 days), and in week 3 of 5.71 mg/day (40 mg/7 days). For regimens of indefinite intervals, the average daily dose is calculated from the average of the high and low values. For example, a regimen that calls for 15 mg every seven to ten days has an average daily dose of 1.82 mg/day $\{(15 \text{ mg}/7 \text{ days}+15 \text{ mg}/10 \text{ days})/2\}$. Average daily doses are in the range of from, for example, 1 to 25 mg/day, 1 to 50 mg/day, 5 to 50 mg/day, 1 to 100 mg/day, or 1 to 300 mg/day of rifamycin-class antibiotic.

By "average initial daily dose" is meant the dose administered on Day 1 divided by the time until the next administration. For example, a dosing regimen that calls for administration of 10 mg of rifamycin-class antibiotic on Days 1, 8, 10, 14, and 18, has an average initial daily dose of 1.43 mg/day $\{10 \text{ mg}/(8-1)\}$.

By "average daily dose over N subsequent dosing days" is meant the sum of rifamycin-class antibiotic administered in N dosing days subsequent to the day of the initial administration divided by the time over which N+1 dosing days subsequent to the initial administration are made. For example, a dosing regimen that calls for administration of 10 mg of rifamycin-class antibiotic on Days 1, 8, 14, and 23, and 15 mg of rifamycin-class antibiotic on Days 10, 18, and 27, has an average daily dose over three subsequent dosing days of 3.5 mg/day $\{(10+15+10)/(18-8)\}$; an average daily dose over four subsequent dosing days of 3.33 25 mg/day $\{(10+15+10+15)/(23-8)\}$; and an average daily dose over five subsequent dosing days of 3.16 mg/day $\{(10+15+10+15+10)/(27-8)\}$.

By "initial administration" is meant a 4 to 14 day period of administration of a rifamycin-class antibiotic to a mammal to whom a rifamycin-class antibiotic has not been administered in the previous 15 days. Desirably, the rifamycin-class antibiotic has not been administered in the previous 22 days, 1 month, 2-months; or 3 months.

By "dose administered on Day 1" is meant the sum total of all rifamycin-class antibiotic administered over the first 24 hours of the initial administration.

By "dosing day" is meant a day on which a rifamycin-class antibiotic is administered to a mammal to whom a rifamycin-class antibiotic has not been administered in the previous 24 hours, wherein the dose administered on a dosing day is the sum total of all rifamycin-class antibiotic administered over a 24 hour period beginning from the first administration on this day.

The term "mammal" specifically includes humans, cattle, horses, dogs, and cats, but also includes many other species.

By "effective" amount is meant the amount of rifamycin-class antibiotic required to treat or prevent an infection or a disease associated with an infection. The effective amount of a rifamycin-class antibiotic used to practice the invention for therapeutic or prophylactic treatment of conditions caused by or contributed to by a microbial infection varies depending upon the agent used, manner of administration, the age, body weight, and general health of the subject. Ultimately, the attending health care provider will decide the appropriate amount and dosage regimen. Such amount is referred to as an "effective" amount.

By "bacterial infection" is meant the invasion of a host mammal by pathogenic bacteria. For example, the infection may include the excessive growth of bacteria that are normally present in or on the body of a mammal or growth of bacteria that are not normally present in or on the mammal. More generally, a bacterial infection can be any situation in which the presence of a bacterial population(s) is damaging to a host mammal. Thus, a mammal is "suffering" from a bacterial infection when an excessive amount of a bacterial population is present in or on the mammal's body, or when the presence of a bacterial population(s) is damaging the cells or other tissue of the mammal. The bacterial infection may be due to gram positive and/or gram negative bacteria.

By "atherosclerosis" is meant the progressive accumulation of smooth muscle cells, immune cells (e.g., lymphocytes, macrophages, or monocytes), lipid products (e.g., lipoproteins, or cholesterol), cellular waste products, calcium, or other substances within the inner lining of an artery, resulting in the narrowing or obstruction of the blood vessel and the development of atherosclerosis-associated diseases. Atherosclerosis is typically manifested within large and medium-sized arteries, and is often characterized by a state of chronic inflammation within the arteries.

By "atherosclerosis-associated disease" is meant any disorder that is caused by or is associated with atherosclerosis. Typically, atherosclerosis of the coronary arteries commonly causes coronary artery disease, myocardial infarction, coronary thrombosis, and angina pectoris. Atherosclerosis of the arteries supplying the central nervous system frequently provokes strokes and transient cerebral ischemia. In the peripheral circulation, atherosclerosis causes intermittent claudication and gangrene and can jeopardize limb viability. Atherosclerosis of an artery of the splanchnic circulation can cause mesenteric ischemia. Atherosclerosis can also affect the kidneys directly (e.g., renal artery stenosis).

A patient who is being treated for an atherosclerosis-associated disease is one who a medical practitioner has diagnosed as having such a disease. Diagnosis may be by any suitable means. Methods for diagnosing atherosclerosis by measuring systemic inflammatory markers are described, for example, in U.S. Pat. No. 6,040,147, hereby incorporated by reference. Diagnosis and monitoring may employ an electrocardiogram, chest X-ray, echocardiogram, cardiac catheterization, ultrasound (for the measurement of vessel wall thickness), or measurement of blood levels of CPK, CPK-MB, myoglobin, troponin, homocysteine, or C-reactive protein. A patient in whom the development of an atherosclerosis-associated disease is being prevented is one who has not received such a diagnosis. One in the art will understand that these patients may have been subjected to the same tests (electrocardiogram, chest X-ray, etc.) or may have been identified, without examination, as one at high risk due to the presence of one or more risk factors (e.g., family history, hypertension, diabetes mellitus, high cholesterol levels). Thus, prophylactic administration of a rifamycin-class antibiotic is considered to be preventing the development of an atherosclerosis-associated disease.

An atherosclerosis-associated disease has been treated or prevented when one or more tests of the disease (e.g., any of the those described above) indicate that the patient's condition has improved or the patient's risk reduced. In one example, a reduction in C-reactive protein to normal levels indicates that an atherosclerosis-associated disease has been treated or prevented.

An alternative means by which treatment or prevention is assessed includes determination of the presence of an infection of *C. pneumoniae*. Any suitable method may be employed (e.g., determination of *C. pneumoniae* in blood monocytes or in the atheroma itself (e.g., in macrophages or foam cells present in the fatty streak), or detection of *C. pneumoniae* DNA, RNA, or antibodies to *C. pneumoniae* in a biological sample from the patient).

"Antibiotic-associated bacterial diarrhea" means the condition wherein antibiotic therapy disturbs the balance of the microbial flora of the gut, allowing pathogenic organisms such as *C. difficile* to flourish. These organisms cause diarrhea. Antibiotic-associated bacterial diarrhea includes such conditions as *C. difficile* associated diarrhea (CDAD) and pseudomembranous colitis.

"Pseudomembranous colitis," also known as pseudomembranous enterocolitis or enteritis, means the inflammation of the mucous membrane of both small and large intestine with the formation and passage of pseudomembranous material (composed of fibrin, mucous, necrotic epithelial cells and leukocytes) in the stools.

By "autoimmune disease" is meant a disease arising from an immune reaction against self-antigens and directed against the individual's own tissues. Examples of autoimmune diseases include but are not limited to systemic lupus erythematosus, rheumatoid arthritis, myasthenia gravis, and Graves' disease.

By "bacteria" is meant a unicellular prokaryotic microorganism that usually multiplies by cell division.

By "bacteria capable of establishing a cryptic phase" is meant any species whose life cycle includes a persistent, non-replicating, metabolically inactive phase. These species include but are not limited to *C. trachomatis, C. pneumoniae, C. psittaci, C. suis, C. pecorum, C. abortus, C. caviae, C. felis, C. muridarum, N. hartmannellae, W. chondrophila, S. negevensis*, and *P. acanthamoeba*, as well as any other species described in Everett et al. (*Int. J. Syst. Evol. Microbiol.* 49:415-440, (1999)), incorporated herein by reference.

By "chronic disease" is meant a disease that is inveterate, of long continuance, or progresses slowly, in contrast to an acute disease, which rapidly terminates. A chronic disease may begin with a rapid onset or in a slow, insidious manner but it tends to persist for several weeks, months or years, and has a vague and indefinite termination.

By "cryptic phase" is meant the latent or dormant intracellular phase of infection characterized by little or no metabolic activity. The non-replicating cryptic phase is often characteristic of persistent forms of intracellular bacterial infections.

By "elementary body phase" is meant the infectious phase of the bacterial life cycle characterized by the presence of elementary bodies (EBs). EBs are small (300-400 nm), infectious, spore-like forms which are metabolically inactive, non-replicating, and found most often in the acellular milieu. EBs possess a rigid outer membrane which protects them from a variety of physical insults such as enzymatic degradation, sonication and osmotic pressure.

By "immunocompromised" is meant a person who exhibits an attenuated or reduced ability to mount a normal cellular or humoral defense to challenge by infectious agents, e.g., viruses, bacterial, fungi, and protozoa. Persons considered immunocompromised include malnourished patients, patients undergoing surgery and bone narrow transplants, patients undergoing chemotherapy or radiotherapy, neutropenic patients, HIV-infected patients, trauma patients, burn patients, patients with chronic or resistant infections such as those resulting from myelodysplastic syndrome, and the elderly, all of who may have weakened immune systems.

By "inflammatory disease" is meant a disease state characterized by (1) alterations in vascular caliber that lead to an increase in blood flow, (2) structural changes in the microvasculature that permit the plasma proteins and leukocytes to leave the circulation, and (3) emigration of the leukocytes from the microcirculation and their accumulation in the focus of injury. The classic signs of acute inflammation are erythema, edema, tenderness (hyperalgesia), and pain. Chronic inflammatory diseases are characterized by infiltration with mononuclear cells (e.g., macrophages, lymphocytes, and plasma cells), tissue destruction, and fibrosis. Non-limiting examples of inflammatory disease include asthma, coronary artery disease, arthritis, conjunctivitis, lymphogranuloma venerum, and salpingitis.

By "intracytoplasmic inclusion" is meant a replicating reticulate body (RB) that has no cell wall. Such inclusions may be detected, for example, through chlamydiae sample isolation and propagation on a mammalian cell lines, followed by fixing and staining using one of a variety of staining methods including Giemsa staining, iodine staining, and immunofluorescence. These inclusions have a typical round or oval appearance.

By "persistent bacterial infection" is meant an infection that is not completely eradicated through standard treatment regimens using anti-bacterial agents. Persistent bacterial infections are caused by bacteria capable of establishing a cryptic or latent phase of infection and may be classified as such by culturing the bacteria from a patient and demonstrating bacterial survival in vitro in the presence of anti-bacterial agents or by determination of anti-bacterial treatment failure in a patient. As used herein, a persistent infection in a patient includes any recurrence of chlamydial infection, after receiving anti-bacterial treatment, from the same species (e.g., *C. trachoniatis*) more than two times over the period of two or more years or the detection of the cryptic phase of the infection in the patient by the methods described. An in vivo persistent infection can be identified through the use of a reverse transcriptase polymerase chain reaction (RT-PCR) to demonstrate the presence of 16S rRNA transcripts in bacterially infected cells after treatment with anti-bacterial agents (*Antimicrob. Agents Chemother.* 12:3288-3297 (2000)).

As used herein, "non-multiplying" phase or bacteria refers to the non-multiplying growth phase of bacteria. Typically, the non-multiplying bacteria will survive standard antimicrobial therapy (see, e.g., Martinez et al., *Antimicrob. Agents Chemother.* 44:1771-1777 (2000); Riesenfeld et al., *Antimicrob. Agents Chemother.* 41:2059-2060 (1997); Alonso et al., *Microbiology* 145:2857-2862 (1999)).

By "replicating phase" is meant the phase of the bacterial cell cycle characterized by the presence of an RB. The RB is the actively replicating form of the *Chlamydia*. It contains no cell wall and is detected as an inclusion in the cell.

DETAILED DESCRIPTION

The invention provides a dosing regimen for administering rifamycin-class antibiotics that can reduce the occurrence of adverse reactions.

The dosing regimen of the invention features ascending doses of a rifamycin-class antibiotic. The dosing regimen can be useful for the treatment of bacterial infections and diseases related to infection.

Using the regimens disclosed herein, a rifamycin-class antibiotic can be used to treat atherosclerosis or diseases associated therewith, sexually transmitted diseases caused, for example, by *C. trachomatis* or *N. gonorrhoeae*, otitis media and other ear infections, antibiotic-associated colitis, gastritis and ulcers associated with an infection of *H. pylori*, community-acquired pneumonia, upper and lower respiratory tract infections, skin and soft tissue infections, bone and joint infections, hospital-acquired lung infections, urinary tract infections, pyelonephritis, intra-abdominal infections, bacterial sepsis, would infections, peritonitis, osteomyelitis, infections after burns, pelvic inflammatory disease, and diseases associated with chronic infections.

Other Therapeutic Agents

The ascending dose regimens described herein may also include a second therapeutic agent, including for example, another antibiotic, an anesthetic, an antimicrobial agent, a zinc salt, or an anti-inflammatory agent (e.g., an non-steroidal anti-inflammatory or a steroid).

Antibiotics that can be combined with a rifamycin-class antibiotic administered in ascending doses include: aminoglycosides, such as amikacin, apramycin, arbekacin, bambermycins, butirosin, dibekacin, dihydrostreptomycin, fortimicin(s), fradiomycin, gentamicin, ispamicin, kanamycin, micronomicin, neomycin, neomycin undecylenate, netilmicin, paromomycin, ribostamycin, sisomicin, spectinomycin, streptomycin, streptonicozid, and tobramycin; amphenicols, such as azidamfenicol, chloramphenicol, chloramphenicol palmirate, chloramphenicol pantothenate, florfenicol, and thiamphenicol; β-Lactams, such as amidinocillin, amdinocillin, pivoxil, amoxicillin, ampicillin, aspoxicillin, azidocillin, azlocillin, bacampicillin, benzylpenicillinic acid, benzylpenicillin, carbenicillin, carfecillin, carindacillin, clometocillin, cloxacillin, cyclacillin, dicloxacillin, diphenicillin, epicillin, fenbenicillin, floxicillin, hetacillin, lenampicillin, metampicillin, methicillin, mezlocillin, nafcillin, oxacillin, penamecillin, penethamate hydriodide, penicillin G benethamine, penicillin G benzathine, penicillin G benzhydrylamine, penicillin G calcium, penicillin G hydragamine, penicillin G potassium, penicillin G, procaine, penicillin N, penicillin O, penicillin V, penicillin V benzathine, penicillin V hydrabamine, penimepicycline, phenethicillin, piperacillin, pivapicillin, propicillin, quinacillin, sulbenicillin, talampicillin, temocillin and ticarcillin; carbapenems, such as imipenem; cephalosporins, such as 1-carba (dethia) cephalosporin, cefactor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpirimide, cefpodoxime proxetil, cefroxadine, cefsulodin, ceftazidime, cefteram, ceftezole; ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin, cephalothin, cefaclor, cefotetan, cefprozil, loracarbef, cefetamet, and cefepime; cephamycins such as cefbuperazone, cefmetazole, cefminox, cefetan, and cefoxitin; monobactams such as aztreonam, carumonam, and tigemonan; oxacephems such as flomoxef and moxolactam; lincosamides such as clindamycin and lincomycin; macrolides such as azithromycin, carbomycin, clarithromycin, erythromycin(s) and derivatives, josamycin, leucomycins, midecamycins, miokamycin, oleandomycin, primycin, rokitamycin, rosaramicin, roxithromycin, spiramycin and troleandomycin; polypeptides such as amphomycin, bacitracin, capreomycin, colistin, enduracidin, enylomycin, fusafungine, gramicidin(s), gramicidin S, mikamycin, polymyxin, polymyxin β-methanesulfonic acid, pristinamycin, ristocetin, teicoplanin, thiostrepton, tuberactinomycin, tyrocidine, tyrothricin, vancomycin, viomycin(s), virginiamycin and zinc bacitracin; tetracyclines such as spicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, senociclin and tetracycline; and 2,4-diaminopyrimidines such as brodimoprim, tetroxoprim and trimethoprim; nitrofurans such as furaltadone, furazolium, nifuradene, nifuratel, nifurfoline, nifurpirinol, nifurprazine, nifurtoinol and nitrofurantoin; quinolones such as amifloxacin, cinoxacin, ciprofloxacin, difloxacin, enoxacin, fleroxacin, flumequine, lomefloxacin, miloxacin, nalidixic acid, norfloxacin, ofloxacin, oxolinic acid, perfloxacin, pipemidic acid, piromidic acid, rosoxacin, temafloxacin, and tosufloxacin; sulfonamides such as acetyl sulfamethoxypyrazine, acetyl sulfisoxazole, azosulfamide, benzylsulfamide, chloramine-β, chloramine-T, dichloramine-T, formosulfathiazole, $N_2$-formyl-sulfisomidine, $N_4$-β-D-glucosylsulfanilamide, mafenide, 4'-(methyl-sulfamoyl) sulfanilanilide, p-nitrosulfathiazole, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine,-sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, sulfanilamidomethanesulfonic acid triethanolamine salt, 4-sulfanilamidosalicyclic acid, $N_4$-sulfanilylsulfanilamide, sulfanilylurea, N-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine and sulfisoxazole; sulfones, such as acedapsone, acediasulfone, acetosulfone, dapsone, diathymosulfone, glucosulfone, solasulfone, succisulfone, sulfanilic acid, p-sulfanilylbenzylamine, p,p'-sulfonyldianiline-N, N'digalactoside, sulfoxone and thiazolsulfone; lipopeptides such as daptomycin; oxazolidones such as linezolid; ketolides such as telithromycin; and miscellaneous antibiotics such as clofoctol, hexedine, magainins, methenamine, methenamine anhydromethylene-citrate, methenamine hippurate, methenamine mandelate, methenamine sulfosalicylate, nitroxoline, squalamine, xibomol, cycloserine, mupirocin, and tuberin.

Preferred non-steroidal anti-inflammatory agents include, for example, detoprofen, diclofenac, diflunisal, etodolac, fenoprofen, flurbiprofen, indomethacin, ketoprofen, mechlofenameate, mefenamic acid, meloxicam, nabumeone, naproxen sodium, oxaprozin, piroxicam, sulindac, tolmeting, celecoxib, rofecoxib, choline salicylate, salsate, sodium salicylate, magnesium salicylate, aspirin, ibuprofen, paracetamol, acetaminophen, and pseudoephedrine, and preferred steroids include, for example, hydrocortisone, prednisone, fluprednisolone, triamcinolone, dexamethasone, betamethasone, cortisone, prednilosone, methylprednisolone, fluocinolone acetonide, flurandrenolone acetonide, and fluorometholone.

Preferred anesthetics include, for example, benzocaine, butamben picrate, tetracaine, dibucaine, prilocaine, etidocaine, mepivacaine, bupivicaine, and lidocaine.

Preferred zinc salts include, for example, zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, and zinc glycinate.

All of the therapeutic agents employed in the methods of the invention can be used in the dose ranges currently known and used for these agents. Different concentrations may be employed depending on the clinical condition of the patient, the goal of therapy (treatment or prophylaxis), the anticipated duration, and the severity of the infection or disease for which ascending doses of a rifamycin-class antibiotic are being administered. Additional considerations in dose selection include the type of infection, age of the patient (e.g., pediatric, adult, or geriatric), general health, and comorbidity. Determining what concentrations to employ are within the skills of the pharmacist, medicinal chemist, or medical practitioner formulating the rifamycin-class antibiotic in combination with other therapeutic agents.

Therapy

The ascending dose regimens described herein can be used to treat or prevent bacterial infections as well as diseases associated with bacterial infections.

Bacterial infections that can be treated or prevented include, for example, respiratory tract infections (e.g., inhalation anthrax), acute bacterial otitis media, bacterial pneumonia, urinary tract infections, complicated infections, non-complicated infections, pyelonephritis, intra-abdominal infections, deep-seated abcesses, bacterial sepsis, skin and skin structure infections (e.g., cutaneous anthrax), soft tissue infections (e.g., endometritis), bone and joint infections (e.g., osteomyelitis, septic arthritis), central nervous system infections (e.g., meningitis), bacteremia, wound infections, peritonitis, meningitis, infections after burn, urogenital tract infections, gastro-intestinal tract infections (e.g., antibiotic-associated colitis, gastrointestinal anthrax), pelvic inflammatory disease, and endocarditis.

Diseases Associated with Infections

Diseases associated with bacterial infections include, but are not limited to, atherosclerosis, multiple sclerosis, rheumatoid arthritis, diabetes, Alzheimer's disease, asthma, cirrhosis of the liver, psoriasis, meningitis, cystic fibrosis, cancer, and osteoporosis.

Several lines of evidence have led to the establishment of a link between bacterial infections and a broad set of inflammatory, autoimmune, and immune deficiency diseases. Thus, the present invention describes methods for treating chronic diseases associated with a persistent infection, such as autoimmune diseases, inflammatory diseases and diseases that occur in immuno-compromised individuals by treating the non-multiplying form of the infection in an individual in need thereof, by administering, in ascending doses, a rifamycin-class antibiotic, or a rifamycin-class antibiotic in conjunction with an antibiotic effective against multiplying bacteria. Progress of the treatment can be evaluated, using the diagnostic tests known in the art, to determine the presence or absence of the bacteria. Physical improvement in the conditions and symptoms typically associated with the disease to be treated can also be evaluated. Based upon these evaluating factors, the physician can maintain or modify the anti-bacterial therapy accordingly.

The therapies described herein can be used for the treatment of chronic immune and autoimmune diseases when patients are demonstrated to have a bacterial infection. These diseases include, but are not limited to, chronic hepatitis, systemic lupus erythematosus, arthritis, thyroidosis, scleroderma, diabetes mellitus, Graves' disease, Beschet's disease, and graft versus host disease (graft rejection). The therapies of this invention can also be used to treat any disorders in which a bacterial infection is a factor or co-factor.

Thus, the present invention can be used to treat a range of disorders in addition to the above immune and autoimmune diseases when demonstrated to be associated with chlamydial infection by the methods of detection described herein; for example, various infections, many of which produce inflammation as primary or secondary symptoms, including, but not limited to, sepsis syndrome, cachexia, circulatory collapse and shock resulting from acute or chronic bacterial infection, acute and chronic parasitic and/or infectious diseases from bacterial, viral or fungal sources, such as a HIV, AIDS (including symptoms of cachexia, autoimmune disorders, AIDS dementia complex and infections) can be treated.

Among the various inflammatory diseases, there are certain features that are generally agreed to be characteristic of the inflammatory process. These include fenestration of the microvasculature, leakage of the elements of blood into the interstitial spaces, and migration of leukocytes into the inflamed tissue. On a macroscopic level, this is usually accompanied by the familiar clinical signs of erythema, edema, tenderness (hyperalgesia), and pain. Inflammatory diseases, such as chronic inflammatory pathologies and vascular inflammatory pathologies, including chronic inflammatory pathologies such as aneurysms, hemorrhoids, sarcoidosis, chronic inflammatory bowel disease, ulcerative colitis, and Crohn's disease and vascular inflammatory pathologies, such as, but not limited to, disseminated intravascular coagulation, atherosclerosis, and Kawasaki's pathology are also suitable for treatment by methods described herein. The invention can also be used to treat inflammatory diseases such as coronary artery disease, hypertension, stroke, asthma, chronic hepatitis, multiple sclerosis, peripheral neuropathy, chronic or recurrent sore throat, laryngitis, tracheobronchitis, chronic vascular headaches (including migraines, cluster headaches and tension headaches) and pneumonia when demonstrated to be pathogenically related to a bacterial infection.

Treatable disorders when associated with a bacterial infection also include, but are not limited to, neurodegenerative diseases, including, but not limited to, demyelinating diseases, such as multiple sclerosis and acute transverse myelitis; extrapyramidal and cerebellar disorders, such as lesions of the corticospinal system; disorders of the basal ganglia or cerebellar disorders; hyperkinetic movement disorders such as Huntington's Chorea and senile chorea; drug-induced movement disorders,,such as those induced by drugs which block CNS dopamine receptors; hypokinetic movement disorders, such as-Parkinson's disease; progressive supranucleo palsy; cerebellar and spinocerebellar disorders, such as astructural lesions of the cerebellum; spinocerebellar degenerations (spinal ataxia, Friedreich's ataxia, cerebellar cortical degenerations, multiple systems degenerations (Mencel, Dejerine-Thomas, Shi-Drager, and Machado-Joseph)); and systemic disorders (Refsum's disease, abetalipoprotemia, ataxia, telangiectasia, and mitochondrial multi-system disorder); demyelinating core disorders, such as multiple sclerosis, acute transverse myelitis; disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; senile dementia of Lewy body type; Wernicke-Korsakoff syndrome; chronic alcoholism; Creutzfeldt-Jakob disease; subacute sclerosing panencephalitis, Hallerrorden-Spatz disease; and dementia pugilistica.

It is also recognized that malignant pathologies involving tumors or other malignancies, such as, but not limited to leukemias (acute, chronic myelocytic, chronic lymphocytic and/or myelodyspastic syndrome); lymphomas (Hodgkin's and non-Hodgkin's lymphomas, such as malignant lymphomas (Burkitt's lymphoma or mycosis fungoides)); carcinomas (such as colon carcinoma) and metastases thereof; cancer-related angiogenesis; infantile hemangiomas; and alcohol-induced hepatitis. Ocular neovascularization, psoriasis, duodenal ulcers, and angiogenesis of the female reproductive tract, can also be treated when demonstrated to be associated with a bacterial infection.

Administration and Formulation

The invention features a method of reducing adverse reactions caused by rifamycin-class antibiotics. The method of the present invention can be used to administer rifamycin-class antibiotics by any method, for example, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral delivery. The method of the present invention may be applied to treating mammals with a pharmaceutical comprising a rifamycin-class antibiotic and a pharmaceutically acceptable diluent, carrier, or excipient, in unit dosage form.

Therapeutic formulations may, for example, be in the form of liquid solutions or suspensions; for oral administration, exemplary formulations may be in the form of tablets or capsules; and for intranasal formulations, in the form of powders, nasal drops, or aerosols.

Methods well known in the art for making formulations are found, for example, in "Remington: The Science and Practice of Pharmacy" (20th ed., ed. A. R. Gennaro, 2000, Lippincott Williams & Wilkins). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycholate and deoxycholate, or may be oily solutions for administration in the form of nasal drops, or as a gel. The concentration of the compound in the formulation will vary depending upon a number of factors, including the dosage of the drug to be administered, and the route of administration.

The rifamycin-class antibiotic may be optionally administered as a pharmaceutically acceptable salt, such as a non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric-acid, hydrobromic acid, sulfuric acid phosphoric acid, or the like. Metal complexes include zinc, iron, and the like.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc). Formulations for oral use may also be provided as chewable tablets.

Administration of compounds in controlled release formulations is useful where the rifamycin-class antibiotic has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window in the gastro-intestinal tract; or (iii) a short biological half-life, so that frequent dosing during a day is required in order to sustain the plasma level at a therapeutic level.

Many strategies can be pursued to obtain controlled release in which the rate of release outweighs the rate of metabolism of the therapeutic compound. For example, controlled release can be obtained by the appropriate selection of formulation parameters and ingredients, including, e.g., appropriate controlled release compositions and coatings. Examples include single or multiple unit tablet or capsule compositions, oil solutions, suspensions, emulsions, microcapsules, microspheres, nanoparticles, patches, and liposomes.

Packaging and Instructions

The methods and compositions of the present invention can be disclosed in the form of instructions for the administration of a rifamycin-class antibiotic in an ascending dose regimen. Typically, the method is disclosed to a patient along with the sale or distribution of a rifamycin-class antibiotic. In some instances, instructions may be included on a label or on a package insert accompanying a kit containing a rifamycin-class antibiotic. The method of the present invention can be incorporated into a prepackaged therapeutic regimen designed to deliver ascending doses of rifamycin-class antibiotics to a patient using the prepackaged regimen. For example, a rifamycin-class antibiotic can be packaged in dosage units containing varying quantities of rifamycin-class antibiotic along with instructions to the patient to administer the smaller quantities followed by the larger quantities over a particular time period. Such doses may consist of one or more tablets, pills, capsules, or caplets.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

EXAMPLE 1

10 mg Rifalazil Twice Weekly in a Non-Ascending Regimen

Rifalazil is administered to a human subject in doses of 10 mg each on Days 1, 4, 8, 11, 15, 18, 22, and 25. The subject is monitored for adverse experiences, including flu-like syndrome. The average daily dose of rifalazil given in week 1 of the regimen is 2.85 mg/day. The average daily dose of rifalazil given in weeks 2-4 is 2.85 mg/day. The average initial daily dose is 3.33 mg/day. The average daily dose over two subsequent dosing days is 2.85 mg/day. The average daily dose over five subsequent dosing days is 2.78 mg/day.

EXAMPLE 2

5 mg Rifalazil Once Weekly in Week 1, 5 mg Twice Weekly Thereafter

Rifalazil is administered to a human subject in doses of 5 mg each on Days 1, 8, 11, 15, 18, 22, and 25. The subject is monitored for adverse experiences, including flu-like syndrome. The average daily dose of rifalazil given in week 1 of the regimen is 0.714 mg/day. The average daily dose of rifalazil given in weeks 2-4 is 1.43 mg/day. The average initial daily dose is 0.714 mg/day. The average daily dose over three subsequent dosing days is 1.5 mg/day.

EXAMPLE 3

12.5 mg Rifalazil Once Weekly in Week 1, 12.5 mg Twice Weekly Thereafter

Rifalazil is administered to a human subject in doses of 12.5 mg each on Days 1, 8, 11, 15, 18, 22, and 25. The subject is monitored for adverse experiences, including flu-like syndrome. The average daily dose of rifalazil given in week 1 of the regimen is 1.79 mg/day. The average daily dose of rifalazil given in weeks 2-4 is 3.57 mg/day. The average initial daily dose is 1.79 mg/day. The average daily dose over three subsequent dosing days is 3.75 mg/day.

EXAMPLE 4

12.5 mg Rifalazil Twice Weekly in Week 1, 25 mg Twice Weekly in Week 2, 50 mg Weekly Thereafter

Rifalazil is administered to a human subject in doses of 12.5 mg each on Days 1 and 4; 25 mg each on Days 8 and 11; and 50 mg each on Days 15 and 22. The subject is monitored for adverse experiences, including flu-like syndrome. The average daily dose of rifalazil given in week 1 of the regimen is 3.57 mg/day. The average daily dose of rifalazil given in week 2 is 7.14 mg/day. The average daily dose of rifalazil given thereafter is 7.14 mg/day. The average initial daily dose is 4.12 mg/day. The average daily dose over three subsequent dosing days is 5.68 mg/day.

EXAMPLE 5

12.5 mg Rifalazil Twice Weekly in Week 1, 25 mg Twice Weekly in Week 2, 50 mg Twice Weekly Thereafter

Rifalazil is administered to a human subject in doses of 12.5 mg each on Days 1 and 4; 25 mg each on Days 8 and 11; and 50 mg each on Days 15, 18, and 22. The subject is monitored for adverse experiences, including flu-like syndrome. The average daily dose of rifalazil given in week 1 of the regimen is 3.57 mg/day. The average daily dose of rifalazil given in week 2 is 7.14 mg/day. The average daily dose of rifalazil given thereafter is 14.29 mg/day. The average initial daily dose is 4.12 mg/day. The average daily dose over three subsequent dosing days is 5.68 mg/day.

EXAMPLE 6

5 mg Rifalazil on Days 1 and 4, 10 mg Rifalazil on Days 9, 12, 15, 18, 21, and 24

Rifalazil is administered to a human subject in doses of 5 mg each on Days 1 and 4 and 10 mg each on Days 9, 12, 15, 18, 21, and 24. The subject is monitored for adverse experiences, including flu-like syndrome. The average daily dose of rifalazil given in week 1 of the regimen is 1.43 mg/day. The average daily dose of rifalazil given in week 2 is 2.85 mg/day. The average daily dose of rifalazil given in week 3 is 4.29 mg/day. The average initial daily dose is 1.66 mg/day. The average daily dose over two subsequent dosing days is 1.87 mg/day. The average daily dose over three subsequent dosing days is 2.27 mg/day. The average daily dose over four subsequent dosing days is 2.5 mg/day.

EXAMPLE 7

5 mg Rifalazil Once Weekly in Week 1, 5 mg Twice Weekly Thereafter in Parallel with Isoniazid

Rifalazil is administered to a human subject in doses of 5 mg each on Days 1, 8, 11, 15; 18, 22, and 25. Concurrently, isoniazid is administered in doses of 900 mg each on Day 1, 4, 8, 11, 15, 18, 22, and 25. The subject is monitored for adverse experiences, including flu-like syndrome. The average daily dose of rifalazil given in week 1 of the regimen is 0.714 mg/day. The average daily dose of rifalazil given in weeks 2-4 is 1.43 mg/day. The average initial daily dose is 0.714 mg/day. The average daily dose over three subsequent dosing days is 1.5 mg/day.

EXAMPLE 8

150 mg Rifampin Twice Weekly in Week 1, 600 mg Twice Weekly Thereafter in Parallel with Isoniazid

Rifampin is administered to a human subject in doses of 150 mg each on Day 1 and 4; and 600 mg each on Days 8, 11, 15, 18, 22, and 25. Concurrently, isoniazid is administered in doses of 900 mg each on Day 1, 4, 8, 11, 15, 18, 22, and 25. The subject is monitored for adverse experiences, including flu-like syndrome. The average daily dose of rifampin given in week 1 of the regimen is 42.85 mg/day. The average daily dose of rifampin given in weeks 2-4 is 171.4 mg/day. The average initial daily dose is 50 mg/day. The average daily dose over three subsequent dosing days is 122 mg/day.

EXAMPLE 9

150 mg Rifapentine Twice Weekly in Week 1, 300 mg Twice Weekly Thereafter in Parallel with Isoniazid Rifapentine is administered to a human subject in doses of 150 mg each on Days 1 and 4; and 300 mg each on Days 8, 11, 15, 18, 22, and 25. Concurrently, isoniazid is administered in doses of 900 mg each on Days 1, 4, 8, 11, 15, 18, 22, and 25. The subject is monitored for adverse experiences, including flu-like syndrome. The average daily dose of rifapentine given in week 1 of the regimen is 42.85 mg/day. The average daily dose of rifapentine given in weeks 2-4 is 85.6 mg/day. The average initial daily dose is 50 mg/day. The average daily dose over three subsequent dosing days is 68.2 mg/day.

EXAMPLE 10

150 mg Rifabutin Twice Weekly in Week 1, 300 mg Twice Weekly Thereafter in Parallel with Isoniazid Rifabutin is administered to a human subject in doses of 150 mg each on Days 1 and 4; and 300 mg each on Days 8, 11, 15, 18, 22, and 25. Concurrently, isoniazid is administered in doses of 900 mg each on Days 1, 4, 8, 11, 15, 18, 22, and 25. The subject is monitored for adverse experiences, including flu-like syndrome. The average daily dose of rifabutin given in week 1 of the regimen is 42.85 mg/day. The average daily dose of rifabutin given in weeks 2-4 is 85.6 mg/day. The average initial daily dose is 50 mg/day. The average daily dose over three subsequent dosing days is 68.2 mg/day.

OTHER EMBODIMENTS

All publications, patent applications, and patents mentioned in this specification are incorporated herein by reference.

While the invention has been described in connection with specific embodiments, it will be understood that it is capable of further modifications. Therefore, this application is intended to cover any variations, uses, or adaptations of the invention that follow, in general, the principles of the invention, including departures from the present disclosure that come within known or customary practice within the art.

Other embodiments are within the claims.

What we claim is:

1. A method of treating bacterial infection in a patient, wherein said patient is already suffering from a bacterial infection, and, said method comprising administering rifalazil to said patient in ascending doses.

2. The method of claim 1, wherein said ascending doses comprise:
    a) an initial administration of an average daily dose for 4 to 14 days; and
    b) following said initial administration, administration of two to four times said average daily dose for 4 to 14 days.

3. The method of claim 1, wherein said ascending doses comprise:
    a) an initial administration of an average daily dose for 4 to 14 days;
    b) following said initial administration, administration of two times said average daily dose for a period of 4 to 14 days; and
    c) following said period, administration of four times said average daily dose for 4 to 14 days.

4. The method of claim 1, wherein said ascending doses comprise an average initial daily dose which is less than 80% of the average daily dose over any of the next two, three, four, or five subsequent dosing days.

5. The method of claim 1, wherein said ascending doses comprise a dose administered on Day 1, said dose administered on Day 1 being less than 90% of the dose administered on any one of the next four dosing days.

6. The method of claim 1, wherein said infection is selected from the group consisting of a community-acquired pneumonia, upper and lower respiratory tract infection, skin and soft tissue infection, bone and joint infection, hospital-acquired lung infection, acute bacterial otitis media, bacterial pneumonia, complicated infection, noncomplicated infection, pyelonephritis, intra-abdominal infection, deep-seated abcess, bacterial sepsis, central nervous system infection, bacteremia, wound infection, peritonitis, meningitis, infections after burn, urogenital tract infection, gastro-intestinal tract infection, pelvic inflammatory disease, endocarditis, and intravascular infection.

7. A method for prophylaxis against bacterial infection resulting from a surgical procedure or implantation of a prosthetic device, said method comprising administering to a patient in need thereof rifalazil in ascending doses.

8. The method of claim 1, wherein said infection is by a Gram-positive bacterium.

9. The method of claim 8, wherein said bacterium is a Gram-positive coccus.

10. The method of claim 9, wherein said Gram-positive coccus is drug-resistant.

11. The method of claim 10, wherein said infection is by a bacterium selected from the group consisting of *S. aureus, S. epidermidis, S. pneumoniae, S. pyogenes, Enterococcus spp.,* and *M. catarrhalis.*

12. The method of claim 1, wherein said bacteria are selected from the group consisting of *Streptococcus pneumoniae, Staphylococcus aureus, Streptococcus pyogenes,* and *Enterococcus spp.*

13. The method of claim 1, wherein said ascending doses comprise administration of rifalazil at a dose of less than 25 mg per week for 1-2 weeks followed by greater than 25 mg per week thereafter.

14. The method of claim 13, wherein said ascending doses comprise adminisration of rifalazil at a dose of less than 10 mg per week for 1-2 weeks followed by greater than 10 mg per week thereafter.

15. The method of claim 14, wherein said ascending doses comprise administration of rifalazil at a dose of less than 5 mg per week for 1-2 weeks followed by greater than 5 mg per week thereafter.

16. The method of claim 1, wherein the rifalazil is administered orally.

17. A method for treating a patient having an infection of *Clostridium difficile* in said patient, said method comprising administering rifalazil in ascending doses to said patient in an amount effective to treat said infection.

18. A method for treating an infection of a bacterium having a multiplying form and a non-multiplying form, said method comprising administering to a patient (i) rifalazil; and (ii) a second antibiotic effective against the multiplying form of said bacterium, wherein said rifalazil is administered in an amount and for a duration effective to treat the non-multiplying form of said bacterium and the second antibiotic is administered in an amount and for a duration effective to treat said multiplying form of said bacterium and wherein rifalazil is administered in ascending doses.

19. The method of claim 18, wherein said antibiotic effective against said multiplying form of said bacterium is administered to said patient in an amount and for a duration to reduce the presence of said bacterium in said patient to less than about $10^6$ organisms/mL; and rifalazil is then administered to said patient in an amount and for a duration effective to reduce the presence of said bacterium to or below a level indicative that said infection has been treated.

20. A method of eradicating non-multiplying bacteria not eradicated in a patient following treatment with a first antibiotic, said method comprising administering rifalazil to said patient in an amount and for a duration effective to eradicate said non-multiplying bacteria in said patient, wherein said rifalazil is administered in ascending doses.

21. A method of treating a patient diagnosed as having a chronic disease associated with a bacterial infection caused by bacteria capable of establishing a non-multiplying form phase, said method comprising administering rifalazil to said patient in an amount and for a duration effective to treat said patient, wherein said rifalazil is administered in ascending doses.

22. A method of treating the cryptic phase of a bacterial infection, said method comprising administering rifalazil to said patient in an amount and for a duration effective to treat said cryptic phase of said bacterial infection, wherein said rifalazil is administered in ascending doses.

* * * * *